(12) United States Patent
Furey et al.

(10) Patent No.: US 10,041,896 B2
(45) Date of Patent: Aug. 7, 2018

(54) SENSOR FITTING FOR BIOTECH PROCESS BAG

(71) Applicant: Pendo TECH, Princeton, NJ (US)

(72) Inventors: James F. Furey, Plainsboro, NJ (US); Dennis C. Annarelli, Newton, PA (US)

(73) Assignee: PENDO TECH, Princeton, NJ (US)

( * ) Notice: Subject to any disclaimer, the term of this patent is extended or adjusted under 35 U.S.C. 154(b) by 0 days.

(21) Appl. No.: 15/101,661

(22) PCT Filed: Dec. 5, 2014

(86) PCT No.: PCT/US2014/068866
§ 371 (c)(1),
(2) Date: Jun. 3, 2016

(87) PCT Pub. No.: WO2015/085214
PCT Pub. Date: Jun. 11, 2015

(65) Prior Publication Data
US 2016/0305897 A1    Oct. 20, 2016

Related U.S. Application Data

(60) Provisional application No. 61/912,884, filed on Dec. 6, 2013.

(51) Int. Cl.
| | |
|---|---|
| A61J 1/10 | (2006.01) |
| G01N 27/07 | (2006.01) |
| A61J 1/14 | (2006.01) |
| G01D 11/24 | (2006.01) |
| G01D 11/30 | (2006.01) |
| A61J 1/12 | (2006.01) |

(52) U.S. Cl.
CPC ............ *G01N 27/07* (2013.01); *A61J 1/1481* (2015.05); *G01D 11/24* (2013.01); *G01D 11/245* (2013.01); *G01D 11/30* (2013.01); *A61J 1/12* (2013.01); *A61J 1/1418* (2015.05)

(58) Field of Classification Search
CPC ............ B01F 15/0085; B01F 15/00831; B01F 13/0827; B01F 15/00207; B01F 7/162; C12M 23/14; C12M 27/02; C12M 29/06; G01D 11/30
See application file for complete search history.

(56) References Cited

U.S. PATENT DOCUMENTS

| | | | |
|---|---|---|---|
| RE32,354 E | * | 2/1987 | Savage ................ B65D 77/067 141/349 |
| 6,523,426 B1 | | 2/2003 | Vincent et al. |
| | | | (Continued) |

FOREIGN PATENT DOCUMENTS

| | | | |
|---|---|---|---|
| EP | 2973103 | | 1/2016 |
| WO | WO2013063550 | * | 5/2013 |

*Primary Examiner* — Alesa Allgood
(74) *Attorney, Agent, or Firm* — Hoffmann & Baron, LLP

(57) ABSTRACT

A fluid process application bag includes a flexible film body having an opening, a port plate sealed around the opening of the flexible film body, a sensor fitting and a sensor contained within the sensor fitting. The port plate has a receptacle defining a passage in fluid communication with an interior of the flexible film body and the sensor fitting has a body portion seated within the passage of the receptacle and is coupled to the receptacle. The sensor has at least one probe communicating with the interior of the flexible film body.

11 Claims, 6 Drawing Sheets

(56) References Cited

U.S. PATENT DOCUMENTS

| | | | |
|---|---|---|---|
| 6,852,216 B2 | 2/2005 | Moscaritolo et al. | |
| 7,226,207 B2 | 1/2007 | Feldmeier | |
| 7,329,338 B2 | 2/2008 | Sieth et al. | |
| 7,469,884 B2 | 12/2008 | Terentiev et al. | |
| 7,603,921 B2 | 10/2009 | Baumfalk et al. | |
| 7,832,296 B2 | 11/2010 | Klees et al. | |
| 7,924,169 B2 | 4/2011 | Baumfalk et al. | |
| 8,123,397 B2 | 2/2012 | Baumfalk et al. | |
| 8,292,491 B2 | 10/2012 | Castillo et al. | |
| 8,302,496 B2 | 11/2012 | Furey et al. | |
| 8,544,352 B2 | 10/2013 | Glatzel et al. | |
| 8,550,439 B2 | 10/2013 | Terentiev et al. | |
| 2005/0163667 A1 | 7/2005 | Krause | |
| 2008/0053255 A1 | 3/2008 | Furey et al. | |
| 2009/0290005 A1 | 11/2009 | Wanibe et al. | |
| 2011/0013474 A1 | 1/2011 | Ludwig et al. | |
| 2011/0249526 A1 | 10/2011 | Wong | |
| 2012/0244608 A1 | 9/2012 | Selker et al. | |
| 2012/0301954 A1 | 11/2012 | Ehring et al. | |
| 2013/0029374 A1 | 1/2013 | Eberheim et al. | |
| 2013/0036843 A1 | 2/2013 | Pfauch et al. | |
| 2013/0036844 A1* | 2/2013 | Furey ............... | G01D 11/245 73/866.5 |
| 2013/0121104 A1 | 5/2013 | Castillio et al. | |

\* cited by examiner

SENSOR FITTING FOR BIOTECH PROCESS BAG

CROSS-REFERENCE TO RELATED APPLICATION

This application claims the benefit of U.S. Provisional Application No. 61/912,884, filed Dec. 6, 2013, which is incorporated herein by reference in its entirety for all purposes.

BACKGROUND

Process applications generally involve a series of actions or steps that are taken in a prescribed sequence in the development and/or manufacturing of a product. Such processes are repeatable and predictable, or at least are generally intended to be. In a wide range of fluid handling process applications knowledge of process conductivity or other fluid characteristics is a valuable piece of information. Such measurements are of particular interest in the technology field of biopharmaceutical process applications for both product development and manufacturing.

For example, in order to measure conductivity in a fluid stream, an in-line gauge is traditionally provided somewhere along the fluid flow path. However, the use of an in-line gauge is not optimal in some process applications. For example, when using lightweight flexible tubing, such in-line devices can be bulky, weighty or too intrusive. Alternatively, to measure conductivity and/or temperature in a vessel, a gauge is inserted into a vessel port. However, in a lightweight, collapsible thin-walled vessel, such a bag insertion of a traditional gauge is not optimal Additionally, many fluid process applications in biotechnology require a fluid handling environment with minimal microbial contamination. It is important to ensure that an uncontaminated environment has been maintained throughout the process. Thus, in critical processes, such as production in bioreactors, filtration, chromatography, and formulation and filling of containers or vials, knowledge of the conductivity or other fluid characteristics in the process is critical, but an uncontaminated environment must be maintained.

One method of maintaining an uncontaminated environment is to employ critical assembly elements that are designed for single-use (or limited use). Thus, such an assembly could contain a large variety of components such as flexible tubing, single use process containers, such as plastic/polymeric bags. Such bags are commonly used in biotech processes for storage of fluids and mixing.

These process bags are typically made of polymeric film materials such as polyethylene (PE) film material and are often provided with port plates, which are attached to the film material before the material is made into a bag. The plates are also made of a similar molded polymeric material and are melt-sealed to the film for the required penetrations for tubing, sample ports, etc.

As mentioned above, there is often a need to measure a physical characteristic or parameter, such as conductivity and/or temperature, of the fluid within a process system, and such measurements are typically taken by sensors provided somewhere within the tubing defining the fluid flow path.

However, in certain instances, it would be desirable to measure such characteristic or parameter of the fluid within the process bag, particularly for mixing of fluids with salts for critical processes or making an addition to adjust a parameter of the fluid. However, the polymers used for fabricating innovative plastic in-line conductivity sensors may be of a material that cannot be heat sealed to the film material. Moreover, adhesives or glues of any type would not be desired in such contamination-free environments and would likely not even work. Also, if sterilization is required, many single-use process bags are not compatible with most heat sterilization temperatures so gamma or ethylene oxide (ETO) processing is typically used so the process sensors should be compatible with gamma or ETO processing.

It is therefore desirable to provide a sensor that is suitable for simple and easy removable connection with a biotech process bag, while providing the ability to accurately measure properties, such as conductivity and/or temperature, of the fluid within the bag. Also, the sensor and bag fitting must be easy to use, inexpensive and universally adaptable to numerous applications.

SUMMARY

According to an aspect of the invention, a sensor connection for a fluid process application bag is provided. The fluid process application bag is generally a flexible film body having an opening. A port plate is sealed around the opening of the fluid process application bag and has a receptacle defining a passage in fluid communication with an interior of the fluid process application bag, A sensor fitting having a body portion is seated within the passage of the receptacle and is coupled to the receptacle. A sensor is contained within the sensor fitting and the sensor has at least one probe communicating with the interior of the fluid process application bag.

In a preferred embodiment, the sensor is a conductivity sensor having two or more probes communicating with the interior of the fluid process application bag, wherein a temperature sensor is placed within one of the probes and the conductivity is measured by at least two of the probes.

In one embodiment, the body portion of the sensor fitting includes a threaded portion for threadable engagement with a threaded portion provided in the receptacle of the port plate.

In an alternative embodiment, the body portion of the sensor fitting includes at least one tab extending radially outwardly from the body portion and the receptacle of the port plate includes a discontinuous rib extending radially inwardly into the passage. The tab engages the rib for releasably securing the sensor fitting in the port plate.

In another alternative embodiment, the body portion of the sensor fitting and the receptacle of the port plate include cooperating detent structure for providing snap-fit engagement between the sensor fitting and the port plate. The detent structure may include a sloped flank extending radially outwardly from the body portion of the sensor fitting and an oppositely sloped flank extending radially inwardly into the passage of the receptacle of the port plate.

The sensor fitting preferably includes an O-ring fitted around the body portion, wherein the O-ring provides a seal between the body portion of the sensor fitting and the receptacle of the port plate. Alternatively, the O-ring can be provided in the receptacle at a suitable location so as to provide a seal between the sensor fitting and the receptacle.

In a preferred embodiment, the body portion of the sensor fitting is cup-shaped and has a side wall and a bottom defining an internal compartment for receiving the sensor, wherein at least one of the probes of the sensor extends through the bottom. In this case, the sensor fitting further preferably includes a head portion covering the internal compartment and an electrical lead of the sensor extends through the head portion.

The port plate further preferably includes a skirt portion extending outwardly from the receptacle, wherein the skirt portion is heat sealed to the fluid process application bag.

Features of the disclosure will become apparent from the following detailed description considered in conjunction with the accompanying drawings. It is to be understood, however, that the drawings are designed as an illustration only and not as a definition of the limits of this disclosure.

BRIEF DESCRIPTION OF THE DRAWINGS

FIG. 5a is a plan view of the port plate shown in FIG. 5 taken along line 5a-5a.

DETAILED DESCRIPTION

Figure 1:
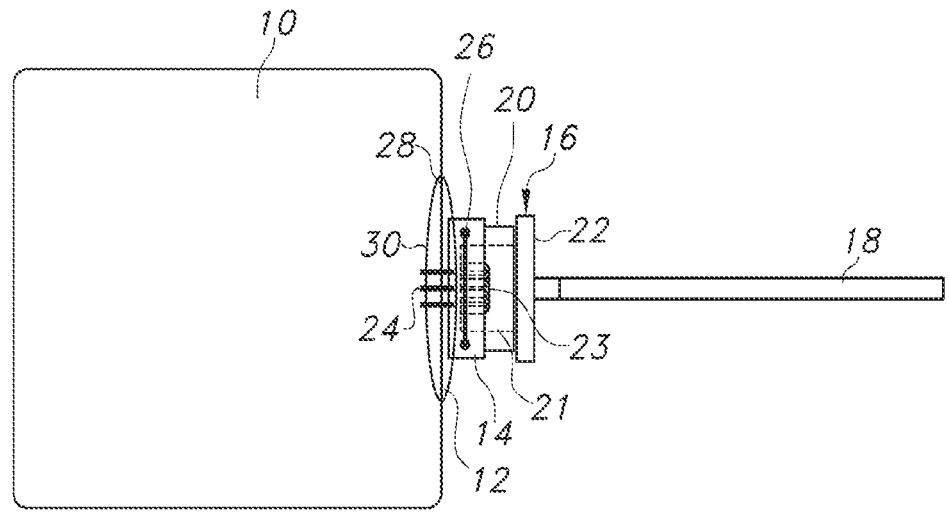
FIG. 1 is an illustration of a sensor fitting attached to a biotech process bag in accordance with the subject invention.
Figure 2:
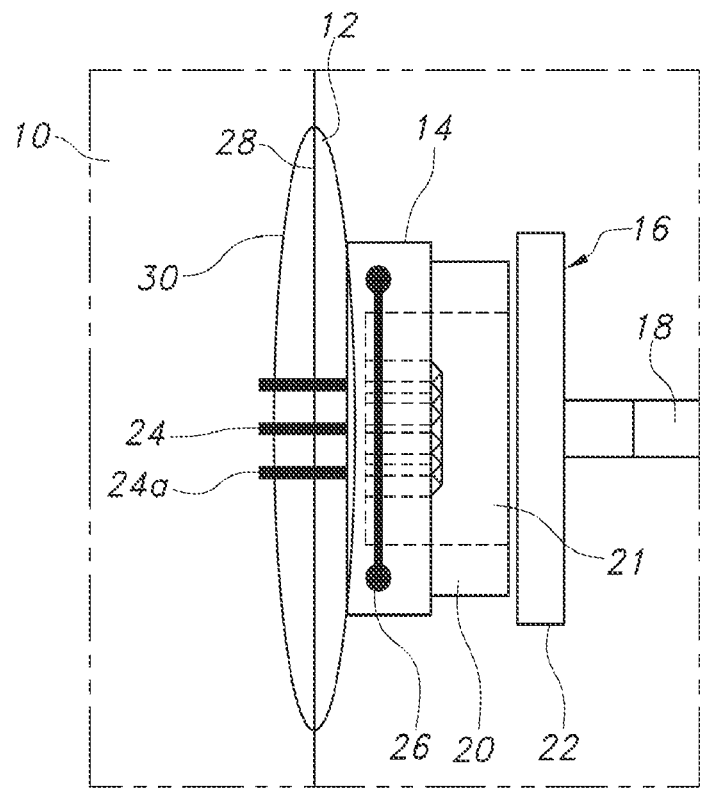
FIG. 2 is an enlarged view of the sensor fitting attached to the biotech process bag shown in FIG. 1.

Looking first at FIGS. 1 and 2, a flexible storage bag 10 is provided with a specially designed port plate 12 having a receptacle 14 to accept a sensor fitting 16 according to the present invention. The sensor fitting 16 may contain any type of sensor desired for measuring a physical property of the fluid within the process bag. Such sensors may include, but are not limited to conductivity sensors, temperature sensors, pressure sensors, pH sensors, and sensors for various types of absorbance measurements, such as UV, visible or near infrared light waves.

The sensor is typically hard wired for suitable connection to external measuring equipment (not shown) via a cable 18. However, other means for communication with the sensor, such as wireless communication or fiber optic connection for light-based measurements, may be employed.

The sensor fitting 16 is somewhat similar to the conductivity sensor connector shown and described in commonly owned U.S. Pat. No. 8,302,496, the specification of which is incorporated herein by reference. However, the sensor fitting 16 of the present invention is specially made without the hose barb/fluid flow portion of the connector disclosed in the '496 patent. Thus, the sensor fitting 16 of the present invention generally includes a body portion 20 and a head portion 22 provided at one end of the body portion, which together form a housing defining an inner compartment for containing the desired sensor therein.

The body portion 20 is cup-shaped with a side wall and a bottom defining a compartment 21 therein for receiving the sensor 23. The head portion 22 may be molded separately from the body portion 20 and may be fixed to the open end of the side wall, opposite the bottom, to seal the compartment 21. The bottom may be provided with suitably sized apertures, through which one or more leads 24 of the sensor can extend and protrude outwardly from the body portion from the compartment.

Thus, the body portion 20 is designed to permit one or more probes or electrodes 24 of the sensor to extend outwardly from one end of the fitting in a fluid-tight manner, while the head portion 22 is designed to permit electrical connection between the external cable 18 and the sensor. In a preferred embodiment shown in the drawings, a conductivity/temperature sensor 23 is shown contained in the sensor fitting 16, which has three (3) conductivity probes 24 protruding from the bottom of the body portion 20 opposite the head portion 22. One probe 24a contains a thermistor, or other temperature measuring element, such as a thermocouple or RTD, of the sensor 23 to measure temperature, while all probes are electrically connected to the conductivity measuring component of the sensor. However, as mentioned above, any type of sensor can be contained within the fitting.

The body portion 20 of the sensor fitting 16 is preferably generally cylindrically shaped and is sized to fit snugly within the correspondingly sized receptacle 14 of the port plate 12. Thus, the sensor fitting 16 is preferably molded with tight tolerances from a high-performance polymer, such as polysulfone, so that the sensor fitting can be inserted and sealed into the receptacle 14 of the port plate 12 to prevent any fluid from leaking around the interface of the sensor.

Figure 4:
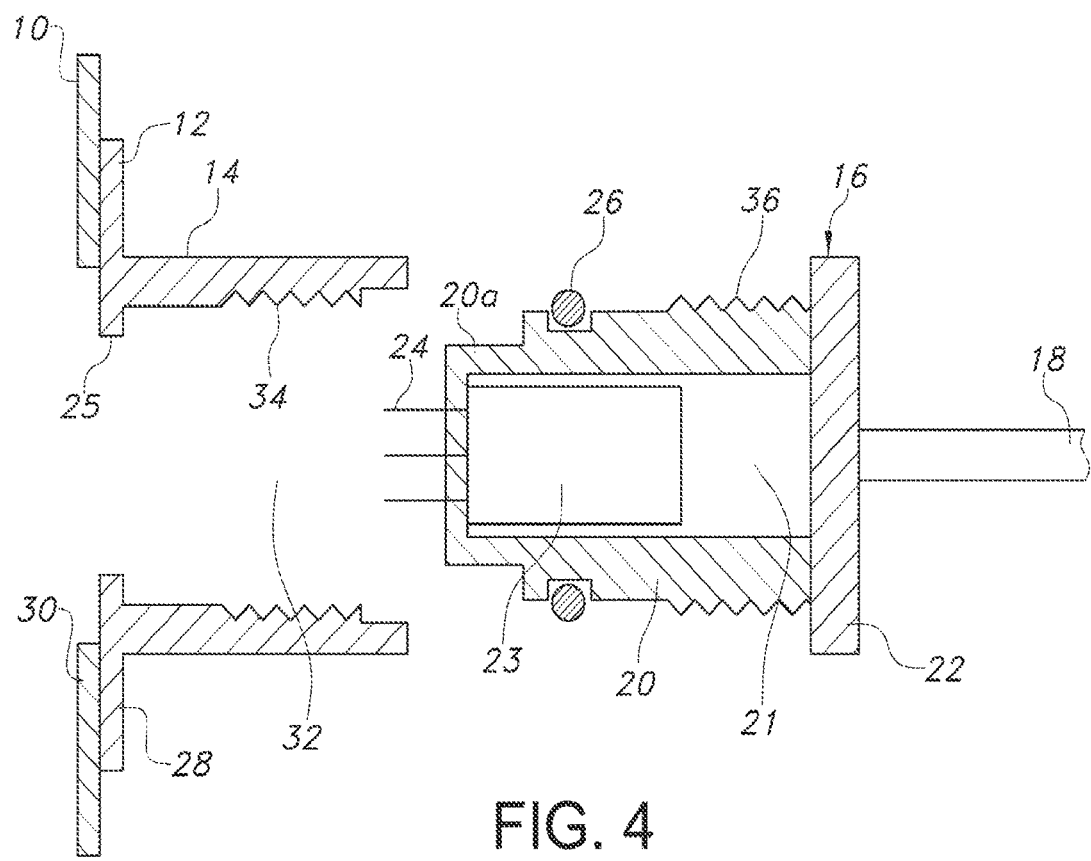
FIG. 4 is a cross-sectional view of a first embodiment of the connection between the sensor fitting and the port plate.

When fully seated in the bottom of the receptacle 14 in the port plate 12, the bottom of the compartment cylinder of the sensor fitting body portion 20 should be as close as possible to be flush with the wall of the bioprocess bag 10 so the electrodes 24 would protrude as much as possible into the bag and not sit in a dead leg. Thus, as shown in FIG. 4, the body portion 20 may be provided with a reduced diameter extension 20a at its bottom that is sized to fit through a hole 25 formed in the port plate. In this manner, the bottom of the sensor fitting will be flush with the wall of the bag and the electrodes 24 will protrude as far as permissible into the bag.

An O-ring 26 is also preferably provided between an inner surface of the receptacle 14 and an outer surface of the sensor fitting body portion 20 so as to provide a fluid tight seal therebetween. The O-ring 26 may be seated in a groove formed in the body portion 20 of the sensor fitting 16 to prevent axial movement of the ring.

Figure 3:
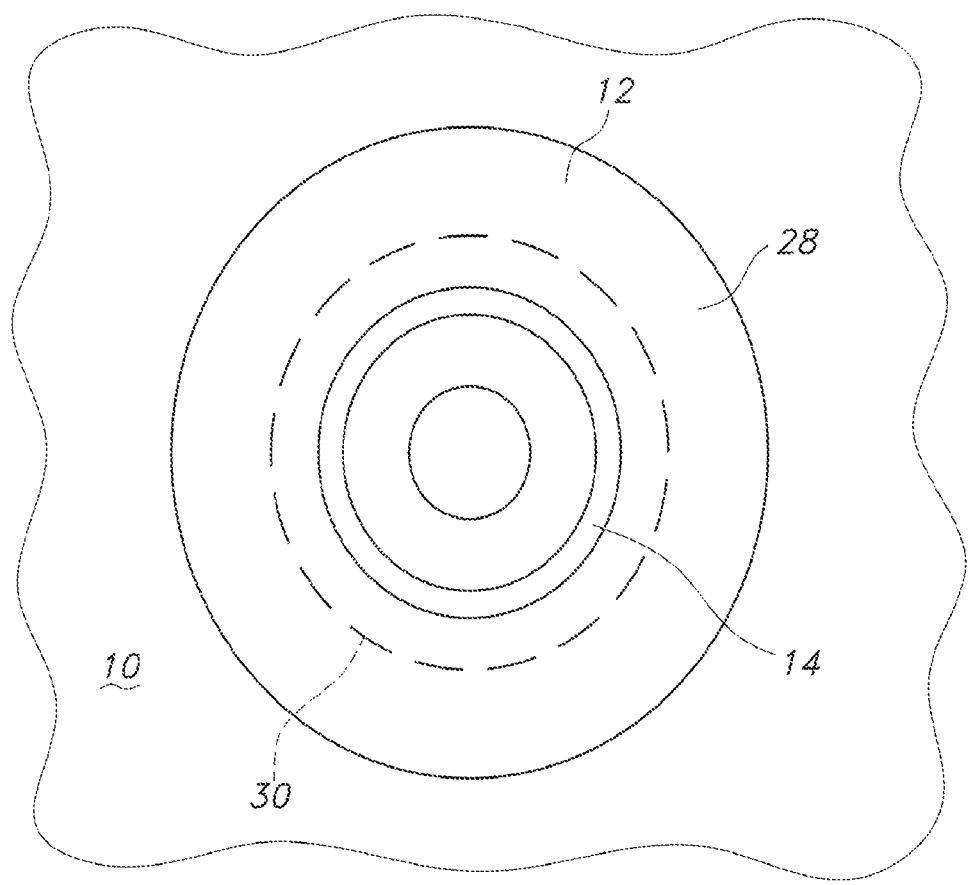
FIG. 3 is a plan view of the port plate shown in FIGS. 1 and 2.

Referring additionally to FIG. 3, the receptacle 14 of the port plate 12 preferably has a circular cross-section and a thin skirt portion 28 of the port plate extends outwardly from the receptacle 14. The skirt portion 28 is heat sealed around a hole 30 formed in the process bag 10 in a conventional manner. The receptacle 14 and skirt portion 28 define an opening 25 communicating with the interior of the process bag 10 via the hole 30 formed in the process bag. The receptacle 14 further forms a passage way 32 communicating with the opening 25 to receive the sensor fitting 12.

The sensor fitting 16 is seated within the passage way 32 and can be attached to the receptacle 14 in several ways. For example, FIGS. 4 and 4a show an embodiment where the inner surface of the receptacle 14 is provided with internal threads 34 and the outer surface of the sensor fitting body portion 20 is provided with external threads 36, which cooperatively engage the internal threads of the receptacle to attach the sensor fitting 16 to the receptacle.

Figure 4A:
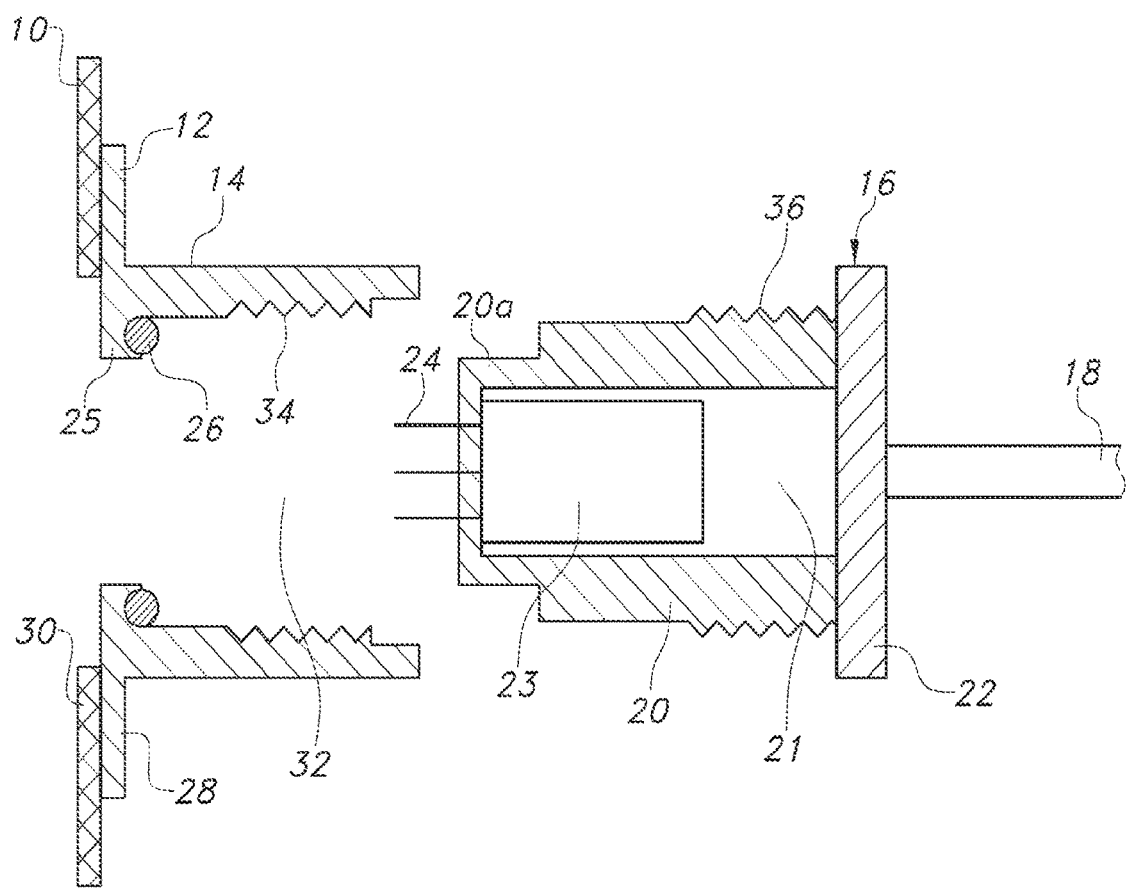
FIG. 4a is a cross-sectional view of the first embodiment shown in FIG. 4 with the O-ring seal provided at a different location.

FIG. 4 shows an O-ring 26 seated in a groove formed in a radial surface of the body portion, while FIG. 4a shows the O-ring seated in a groove formed in a sealing surface of the receptacle. The O-ring 26 of FIG. 4 will seal against an inner radial surface of the receptacle, while the O-ring 26 of FIG. 4a will seal against an axial surface of the sensor fitting.

Figure 5:
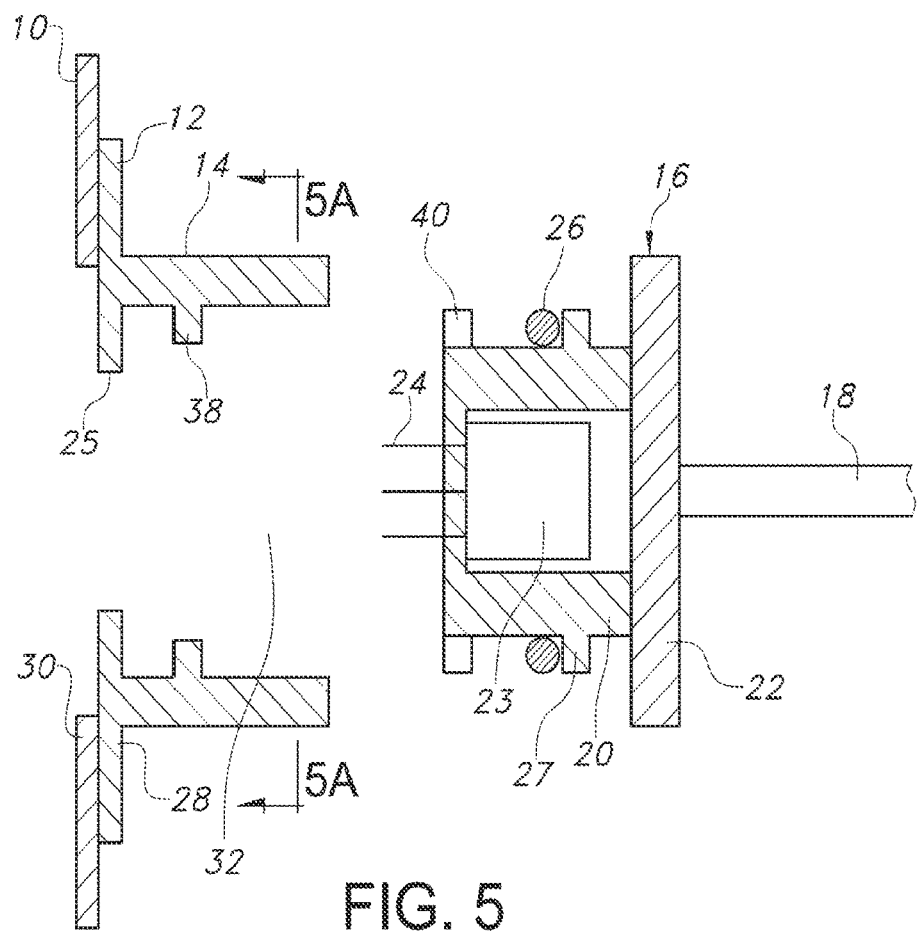
FIG. 5 is a cross-sectional view of a second embodiment of the connection between the sensor fitting and the port plate.
Figure 5A:
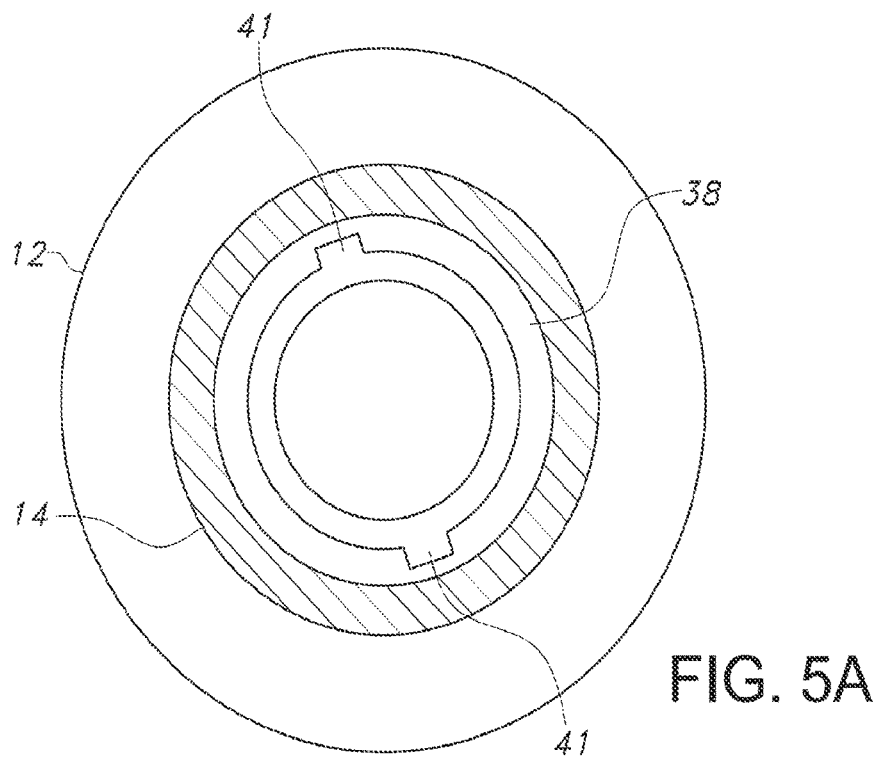

FIGS. 5 and 5a show an alternative embodiment, wherein the inner surface of the receptacle 14 is provided with one or more discontinuous ribs 38 extending radially into the passage way 32, and wherein the outer surface of the sensor body portion 20 is provided with one or more intermittent tabs 40 extending radially outward from the body portion. As can be appreciated from FIG. 5a, the sensor fitting 16 is inserted into the receptacle so that the intermittent tabs 40 pass through gaps 41 of the discontinuous ribs 38 formed in the receptacle. Upon slight rotation of the sensor fitting 16 into the receptacle 14, the ribs 38 engage the tabs 40 in a twist-lock manner to secure the sensor within the receptacle. The O-ring 26 will then be captured between the ribs 38 of the receptacle 14 and a flange 27 provided on the outside surface of the body portion 20 of the fitting.

The structure for providing the twist-lock engagement of FIGS. 5 and 5a can be designed to allow removal of the sensor fitting 16 from the receptacle 14, or additional structure can be provided to ensure permanent engagement between the receptacle and the fitting. For example, a locking tab can be provided that allows only a one-way engagement of the fitting and the receptacle so that removal of the sensor fitting from the receptacle cannot be achieved without damaging one or both elements.

Figure 6:
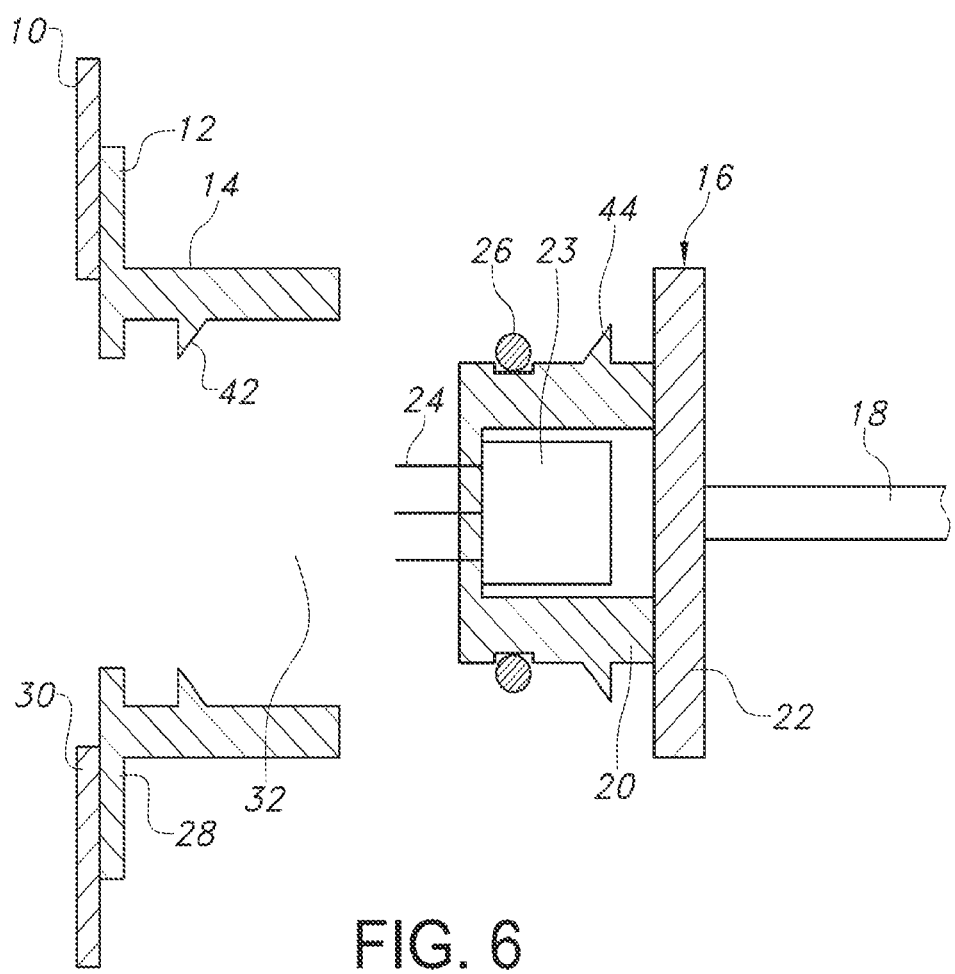
FIG. 6 is a cross-sectional view of a third embodiment of the connection between the sensor fitting and the port plate.

FIG. 6 shows yet another alternative embodiment, wherein the inner surface of the receptacle 14 and the outer surface of the sensor fitting body portion 20 are provided with cooperating detent structure 42, 44 for providing an interference snap fit between the sensor fitting 16 and the receptacle 14 upon insertion of the sensor fitting 16 into the receptacle 14. The detent structure 42, 44 can take the form of ridges having oppositely sloped flanks to permit one-way insertion of the sensor fitting 16 into the receptacle, but which will lock the fitting within the receptacle upon full insertion.

The port plate 12 and the sensor fitting 16 are preferably made of lightweight plastic, such as polyethylene, however other materials can be used that suit a particular application. For example, the port plate 12 and sensor fitting 16 can be made of parts that are compatible with both gamma radiation (using doses high enough for sterilization of process assemblies used in the industry, i.e., up to 45 KGy) or chemical sterilization (such as ethylene oxide (ETO)).

As mentioned above, unlike the sensor connector disclosed in U.S. Pat. No. 8,302,496, the sensor fitting 16 of the present invention does not have inlet and outlet ports with hose barbs for in-line coupling within process tubing. Furthermore the receptacle fitting design of the present invention can be used for many types of sensors to gain access for analytical measurements. The sensors and related portions of the system described herein throughout can likewise be increased in size and/or capacity to provide appropriate measurement for systems of various sizes and performance capabilities.

While various embodiments of the present invention are specifically illustrated and/or described herein, it will be appreciated that modifications and variations of the present invention may be effected by those skilled in the art without departing from the spirit and intended scope of the invention.

What is claimed is:

1. A sensor connection for a fluid process application bag comprising:
    a fluid process application bag having an opening;
    a port plate sealed around said opening of the fluid process application bag, the port plate having a receptacle defining an interior and a skirt portion extending outwardly from the receptacle in a direction away from the interior, the interior defining a passage in fluid communication with an interior of the fluid process application bag;
    a sensor fitting seated within said interior of said receptacle and being coupled to said receptacle, said sensor fitting having a cup-shaped body portion with a side wall and a bottom defining an internal compartment, said bottom being substantially flush with the opening of said fluid process application bag; and
    a sensor contained within said internal compartment of said body portion of said sensor fitting, said sensor having at least one probe extending through said bottom of said body portion in a fluid-tight manner and communicating with an interior of the fluid process application bag,
    wherein said side wall of said body portion of said sensor fitting and said receptacle of said port plate comprise cooperating detent structure for providing snap-fit engagement between said sensor fitting and said port plate.

2. A sensor connection as defined in claim 1, wherein said detent structure comprises a sloped flank extending radially outwardly from said body portion of said sensor fitting and an oppositely sloped flank extending radially inwardly into said interior of said receptacle of said port plate.

3. A sensor connection as defined in claim 1, further comprising an O-ring in sealing engagement between an inner surface of said receptacle and an outer surface of said sensor fitting, said O-ring providing a seal between said body portion of said sensor fitting and said receptacle of said port plate.

4. A sensor connection as defined in claim 1, wherein said skirt portion is heat sealed to said fluid process application bag.

5. A sensor connection as defined in claim 1, wherein said sensor is a conductivity sensor.

6. A sensor connection as defined in claim 5, wherein said conductivity sensor comprises at least two probes communicating with the interior of the fluid process application bag, said at least two probes extending through respective spaced apart apertures provided through the bottom of the cup-shaped body portion of the sensor fitting, within one of said probes an element for measuring temperature is provided and at least two of said probes being used to measure conductivity.

7. A sensor connection as defined in claim 1, wherein said sensor fitting further comprises a head portion covering said internal compartment.

8. A sensor connection as defined in claim 7, wherein an electrical lead of said sensor extends through said head portion.

9. A fluid process application bag comprising:
    a flexible film body having an opening;
    a port plate sealed around said opening of said flexible film body, the port plate having a receptacle defining an interior and a skirt portion extending outwardly from the receptacle in a direction away from the interior, the interior defining a passage in fluid communication with an interior of the flexible film body;

a sensor fitting seated within said interior of said receptacle and being coupled to said receptacle, said sensor fitting having a cup-shaped body portion with a side wall and a bottom defining an internal compartment, said bottom being substantially flush with the opening of said fluid process application bag; and a sensor contained within said internal compartment of said body portion of said sensor fitting, said sensor having at least one probe extending through said bottom of said body portion in a fluid-tight manner and communicating with an interior of the flexible film body, wherein said side wall of said body portion of said sensor fitting and said receptacle of said port plate comprise cooperating detent structure for providing snap-fit engagement between said sensor fitting and said port plate.

10. A fluid process application bag as defined in claim 9, wherein said sensor is a conductivity sensor.

11. A fluid process application bag as defined in claim 10, wherein said conductivity sensor comprises at least two probes communicating with the interior of the fluid process application bag, within one of said probes an element for measuring temperature is provided and at least two of said probes being used to measure conductivity.

* * * * *